US005827715A

United States Patent [19]
Ishii et al.

[11] Patent Number: 5,827,715
[45] Date of Patent: Oct. 27, 1998

[54] HEAT RESISTANT MALTOSE PHOSPHORYLASE, PROCESS FOR PREPARATION THEREOF, BACTERIA USED FOR PREPARATION THEREOF, AND METHODS FOR USING THE ENZYME

[75] Inventors: Keiko Ishii; Yasushi Inoue; Tetsuji Tomita, all of Funabashi, Japan

[73] Assignee: Showa Sangyo Co., Ltd., Tokyo, Japan

[21] Appl. No.: 686,647

[22] Filed: Jul. 26, 1996

[30] Foreign Application Priority Data

Jul. 31, 1995 [JP] Japan ................................. 7-213005

[51] Int. Cl.$^6$ .............................. C12N 9/12; C12N 9/26; C12N 9/34; C12P 19/20
[52] U.S. Cl. .............................. 435/194; 435/96; 435/99; 435/195; 435/200; 435/201; 435/205
[58] Field of Search ..................... 435/194, 200, 435/201, 205, 195, 96, 99

[56] References Cited

U.S. PATENT DOCUMENTS

| | | | |
|---|---|---|---|
| 3,944,470 | 3/1976 | Diehl et al. | 435/188 |
| 4,237,221 | 12/1980 | Gauhl et al. | 435/15 |
| 5,565,341 | 10/1996 | Takahashi et al. | 435/100 |

FOREIGN PATENT DOCUMENTS

| | | |
|---|---|---|
| 60-54036 | 11/1985 | Japan . |
| 63-60998 | 11/1988 | Japan . |
| 1-91778 | 4/1989 | Japan . |
| 5-211882 | 8/1993 | Japan . |
| 5-292986 | 11/1993 | Japan . |
| 6-189779 | 7/1994 | Japan . |
| 7-59584 | 3/1995 | Japan . |
| 7-99988 | 4/1995 | Japan . |
| 7-255473 | 10/1995 | Japan . |
| 7-284389 | 10/1995 | Japan . |
| 7-327691 | 12/1995 | Japan . |
| 8-89273 | 4/1996 | Japan . |
| 8-131157 | 5/1996 | Japan . |
| 8-131166 | 5/1996 | Japan . |
| 8-131182 | 5/1996 | Japan . |
| WO 87/00196 | 1/1987 | WIPO . |

OTHER PUBLICATIONS

Agric. Biol. Chem. vol. 49 No. 7, 1985 pp. 2113–2118 Murao et al "Enzymatic synthesis of Trehalose from Maltose".

Database WPI Week 8920 Derwent AN 89–148138 "New maltose phosphorylase" & JP–A–01 091 778.
Database WPI Derwent AN 96–303845 "Thermally–stable trehalose phosphorylase . . . " & JP 08 131 166.
Taugney et al, FEMS Microbiol. Letters 97:191–196 1992.
Fitting et al, J. Biol. Chem. 63:545–560 (1952).
Wood et al, Biochem. J. 78:204–209 (1961).
Kamogawa et al: *Agr. Biol. Chem.*, 37 (12), 2813–2819, 1973, "Purification and Properties of Maltose Phosphorylase from *Lactobacillus brevis*", pp. 2813–2819.
Nippon Nogei Kagaku Kaishi, 69, (1995) 1Fa14.
Yoshida et al: *Oyo Toshitsu Kagaku*, vol. 42, No. 1, pp. 19–25 (1995), "Production and Application of Maltose Phosphorylase and Trehalose Phosphorylase by a Strain of Plesiomonas", pp. 19–25.
Nippon Nogei Kagaku Kaishi, 68, 580, 1994, p. 246, 3Ra13 and 3Ra14.
Marechal et al: "Metabolism of Trehalose in *Euglena gracilis*," *The Journal of Biological Chemistry*, 247, No. 18, Issue of May 25, pp. 3223–3228, 1972.
Kizawa et al: "Purification and Characterization of Trehalose Phosphorylase from *Micrococcus varians*," *Biosci. Biotech. Biochem.*, 59(10), pp. 1908–1912, 1995.
Aisaka et al: "Production of trehalose phosphorylase by *Catellatospora ferruginea*," *FEMS Microbiology Letters* 131 (1995) pp. 47–51.
Schick et al: "Trehalose phosphorylase from *Pichia fermentans* and its role in he metabolism of trehalose," *Appl Microbiol Biotechnol* (1995)43: pp. 1088–1095.
Hiruma et al: Purification and Some Properties of Maltose Phosphorylase from *Enterococcus hirae* IFO 3181, *Nippon Nogeikagaku Kaishi*, vol. 70, No. 70 pp. 773–780, 1996.

Primary Examiner—Francisco C. Prats
Attorney, Agent, or Firm—Nixon & Vanderhye P.C.

[57] ABSTRACT

This invention relates to heat resistant maltose phosphorylase having an activity of 80% or more of the one untreated after treated in a buffer of pH 6.0, at one temperature of 50° to 60° C. for 15 minutes, a process for preparation thereof, bacteria used for preparation thereof, and processes for preparation of β-glucose-1-phosphoric and trehalose using the enzyme.

By carrying out enzymatic reaction at high reaction temperatures using this enzyme, it is possible to prepare β-glucose-1-phosphoric acid or trehalose industrially advantageously, with lowering of contamination with various germs and shortening of reaction time.

2 Claims, 5 Drawing Sheets

HEAT RESISTANT MALTOSE PHOSPHORYLASE, PROCESS FOR PREPARATION THEREOF, BACTERIA USED FOR PREPARATION THEREOF, AND METHODS FOR USING THE ENZYME

FIELD OF THE INVENTION AND RELATED ART STATEMENT

This invention relates to novel maltose phosphorylase excellent in thermal stability, a process for preparation thereof, bacteria used for its preparation, and methods for use thereof, and more detailedly, relates to novel maltose phosphorylase having high thermal stability which thermophilic bacteria belonging to the genus Bacillus produces, a process for preparation thereof, the thermophilic bacteria, and a process for preparation of β-glucose-1-phosphoric acid or trehalose.

Trehalose is a disaccharide ranging widely over yeasts, molds, bacteria, insects, etc., and is a useful substance whose utilization as a protectant against drying (WO87/00196) is under consideration because it is stabler than other disaccharides.

Heretofore, as processes for preparing trehalose, an extraction process from a yeast (Japanese Published Unexamined Patent Application No. 292986/ 1993), a fermentation process using a bacterium (Japanese Published Unexamined Patent Application No. 211882/1993), etc. have been known. However, as to trehalose prepared in these processes, its preparation cost is heightened, for example because mass production is difficult from the aspects of operation and facilities and impurities—removing steps are complicated, and thus trehalose is very expensive and it has been impossible to utilize it for food use.

On the other hand, enzymatic processes are mentioned as an effective process for preparing trehalose inexpensively. As one example thereof, there is a simultaneous reaction process using maltose phosphorylase and trehalose phosphorylase (Japanese Published Examined Patent Application No. 60998/1988). This process utilizes reactions that the two kinds of phosphorylases act on maltose and trehalose, respectively, to phosphorolyze them reversibly, and thereby glucose and β-glucose-1-phosphoric acid are formed, and is characterized in that both enzymes are simultaneously made to act on maltose as an inexpensive raw material to form trehalose.

As maltose phosphorylases so far known, there can be mentioned those produced by Lactobacillus brevis ATCC 8287 (Agr. Biol. Chem. 37 (12), 2813–2819, 1973), Lactobacillus sanfrancisco (Japanese Published Unexamined Patent Application No. 91778/1989), Lactobacillus brevis DMS 20054, NCIB 8836, 8561 and 8562, Lactobacillus plantarum DMS 20174 and FERM P-4628, Lactobacillus reuteri DMS 20016, Lactobacillus fermentum DMS 20052, Streptococcus spec. FERM P-4624, FERM P-4625, P-4626 and FERM P-4627 (Japanese Published Examined Patent Application No. 54036/1985), and Plesiomonas SH-35 (Nippon Nogei Kagaku Kaishi, 69 (extraordinary extra number), 28, 1995; Oyo Toshitsu Kagaku, 42 (1), 19–25, 1995).

Among them, those whose physicochemical properties are examined are only maltose phosphorylases produced by Lactobacillus brevis ATCC 8287 (Agr. Biol. Chem. 37 (12), 2813–2819, 1973), Lactobacillus sanfrancisco (Japanese Published Unexamined Patent Application No. 91778/1989) and Plesiomonas SH-35 (Nippon Nogei Kagaku Kaishi, 69 (extraordinary extra number), 28, 1995). Any of the thermal stabilities of these enzymes is as low as 40° C. or less, and when trehalose preparation is carried out using these enzymes, there arises a problem that the possibility of contamination with various microorganisms is high during the preparation steps because the reaction temperature is low, and thus it is difficult to utilize them under industrial preparation conditions.

OBJECT AND SUMMARY OF THE INVENTION

As a process for preparing trehalose inexpensively and on an industrial scale, the enzyme process wherein both maltose phosphorylase and trehalose phosphorylase are used and maltose is used as a starting material is thought to be the most effective.

On the other hand, when production by enzymatic reaction is carried out industrially, it is usually adopted to make the reaction temperature higher for the purpose of lowering contamination with various microorganisms . Further , heightening the reaction temperature brings about such advantages, e.g. that charge per unit volume can be increased because the solubilities of the substrate and product are increased, and the reaction time can be shortened because the enzymatic reaction rate is increased, and is advantageous in the aspect of costs.

For preparing trehalose by enzymatic reaction at high temperatures, heat resistant maltose phosphorylase having high thermal stability is required. However, the above-mentioned maltose phosphorylases originating in the genera Lactobacillus and Plesiomonas do not have so high thermal stability.

Thus, enzymes fit for actual high temperature enzymatic reaction, specifically enzymes being stable at 55° C. or more have been desired.

The present inventors had searched for heat resistant maltose phosphorylase producing glucose and β-glucose-1-phosphoric acid from maltose from nature, and as a result, they found out that certain thermophilic bacteria belonging to the genus Bacillus produce well enzymes answering the above purpose, and completed this invention.

They further found that heat resistant maltose phosphorylases produced by liquid culturing these strains can be utilized for preparation of trehalose, if necessary after purification or immobilization. Namely, the invention provides novel heat resistant maltose phosphorylase, a process for preparation thereof, bacteria used for preparation thereof, and processes for preparation of β-glucose-1-phosphoric acid and trehalose.

These objects of the invention have been attained by

1. Heat resistant maltose phosphorylase having an activity of 80% or more of the one untreated after treated in a buffer of pH 6.0, at one temperature of 50° to 60° C. for 15 minutes;

2. Heat resistant maltose phosphorylase having the following enzymological properties:

(1) Action

Phosphorolyze maltose reversibly. Namely, when it is made to act on maltose in the presence of phosphoric acid, it produces glucose and β-glucose-1-phosphoric acid in an equimolar amount, and when it is made to act on glucose and β-glucose-1-phosphoric acid, it produces maltose and phosphoric acid in an equimolar amount.

(2) Substrate specificity

Act specifically on maltose.

(3) Optimum temperature

The optimum temperature of maltose phosphorolysis reaction is from around 55° C. to around 70° C., and it exhibits about 50% or more of the maximum activity in the range of 50° C. to 70° C.

(4) Thermal stability

Have an activity of about 80% of the one untreated after treated in 10 mM acetate buffer (pH 6.0), at 60° C. for 15 minutes.

(5) Optimum pH 6.0 to 7.0.

(6) pH stability

Stable at pH 5.5 to 8.0.

(7) Molecular weight 150,000 to 190,000 when measured by gel filtration chromatography;

3. Heat resistant maltose phosphorylase having the following enzymological properties:

(1) Action

Phosphorolyze maltose reversibly. Namely, when it is made to act on maltose in the presence of phosphoric acid, it produces glucose and β-glucose-1-phosphoric acid in an equimolar amount, and when it is made to act on glucose and β-glucose-1-phosphoric acid, it produces maltose and phosphoric acid in an equimolar amount.

(2) Substrate specificity

Act specifically on maltose.

(3) Optimum temperature

The optimum temperature of maltose phosphorolysis reaction is from around 55° C. to around 70° C., and it exhibits about 50% or more of the maximum activity in the range of 50° C. to 70° C.

(4) Thermal stability

Have an activity of about 80% of the one untreated after treated in 10 mM acetate buffer (pH 6.0), at 60° C. for 15 minutes.

(5) Optimum pH 6.0 to 7.0.

(6) pH stability

Stable at pH 5.5 to 8.0.

(7) Molecular weight 150,000 to 190,000 when measured by gel filtration chromatography.

(8) Inactivation

100% inactivated when heated at 100° C. for 10 minutes.

(9) Isoelectric point 4.7 to 5.1.

(10) Inhibitor

Its activity is strikingly inhibited with $HgCl_2$;

4. A process for preparation of maltose phosphorylase which comprises culturing in a nutrient medium a bacterium which belongs to the genus Bacillus and has the ability to produce maltose phosphorylase, and recovering maltose phosphorylase formed from the culture broth;

5. Bacillus sp. RK-1 (FERM BP-5592) or a mutant thereof having maltose phosphorylase-producing ability;

6. Bacillus sp. MK-1 (FERM BP-5593) or a mutant thereof having maltose phosphorylase-producing ability;

7. A process for preparation of β-glucose-1-phosphoric acid which comprises reacting maltose with phosphoric acid or a phosphate salt in an aqueous medium, at 55° to 70° C., at pH 4.5 to 8.0, in the presence of heat resistant maltose phosphorylase having an activity of 80% or more of the one untreated after treated in a buffer of pH 6.0, at one temperature of 50° to 60° C. for 15 minutes; and 8. A process for preparation of trehalose which comprises reacting maltose with phosphoric acid or a phosphate salt in an aqueous medium, at 55° to 70° C., at pH 4.5 to 8.0, in the presence of heat resistant maltose phosphorylase having an activity of 80% or more of the one untreated after treated in a buffer of pH 6.0, at one temperature of 50° to 60° C. for 15 minutes, and heat resistant trehalose phosphorylase.

DETAILED DESCRIPTION OF THE INVENTION

The enzymological properties of the heat resistant maltose phosphorylase of the invention are as follows. As the heat resistant maltose phosphorylase, one obtained in Example 1 and prepared from Bacillus sp. RK-1 was used.

In this connection, maltose phosphorylase activity was assayed according to the following method. An enzyme solution (0.4 ml), 0.06 ml of 0.5M potassium phosphate-citric acid buffer (pH 6.0), 0.6 ml of 2 w/v % maltose and 0.14 ml of distilled water were mixed, and reaction was carried out at 60° C. for 15 minutes and ceased by boiling for 10 minutes. Then, 0.02 ml of a sample was taken from the reaction-ceased solution, 3 ml of a reagent for glucose examination (Glucose CII-Test Wako; Wako Pure Chemical Industries, Ltd.) was added, reaction was carried at room temperature for 20 minutes, the absorbance at 505 nm was measured using a spectrophotometer, and the amount of glucose formed in the reaction solution was determined from the measured value. From the amount of the formed glucose, the amount of the enzyme necessitated to phosphorolyze 1 μmol of maltose in one minute is calculated, and was assumed to be 1 unit.

Further in order to confirm the enzyme is phosphorylase, the reaction solution after completion of the reaction was separated using an anion exchange column, and subjected to high performance liquid chromatography using a refraction index detector as a detecting means to determine β-glucose-1-phosphoric acid.

(1) Action

Phosphorolyze maltose reversibly, as shown in Formula (1). Namely, when it is made to act on maltose in the presence of phosphoric acid, it produces glucose and β-glucose-1-phosphoric acid in an equimolar amount, and when it is made to act on glucose and β-glucose-1-phosphoric acid, it produces maltose and phosphoric acid in an equimolar amount.

maltose+phosphoric acid⇌glucose+β-glucose-1-phosphoric acid (1)

(2) Substrate specificity

Phosphorolysis reaction was carried out using trehalose, neotrehalose, maltose, isomaltose, cellobiose, sucrose, p-nitrophenyl-α-D-glucoside, p-nitrophenyl-β-D-glucoside, etc. as substrates, and as a result, formation of glucose was scarcely observed except maltose (Table 1).

(3) Optimum temperature

Figure 1:
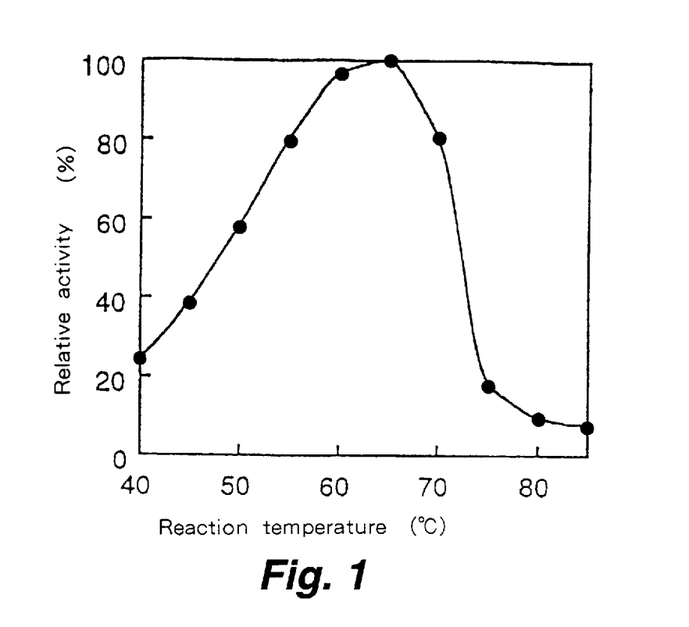
FIG. 1 shows the optimum temperature of a heat resistant maltose phosphorylase obtained in the invention.

Reaction was carried out in 25 mM potassium phosphate-citric acid buffer (pH 6.0) at various temperatures (40° to 85° C.), and as a result, the optimum temperature of maltose phosphorolysis reaction was from around 55° C. to around 70° C., and the enzyme exhibited about 50% or more of the maximum activity in the range of 50° to 70° C. (FIG. 1).

(4) Thermal stability

Figure 2:
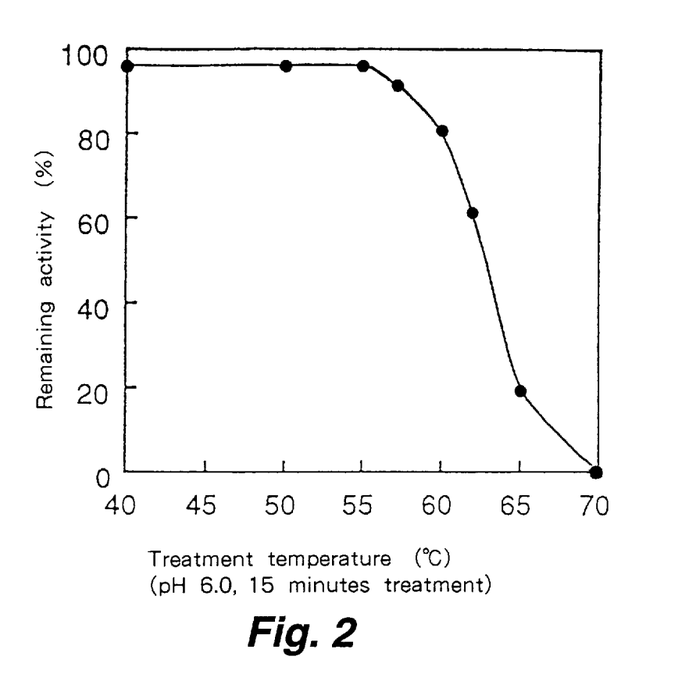
FIG. 2 shows the thermal stability of the heat resistant maltose phosphorylase obtained in the invention.

The enzyme was incubated in 10 mM acetate buffer (pH 6.0) and the remaining activity was assayed, and as a result, it exhibited an activity of 80% or more of the one untreated after treatment at 60° C. for 15 minutes (FIG. 2).

(5) Optimum pH

Figure 3:
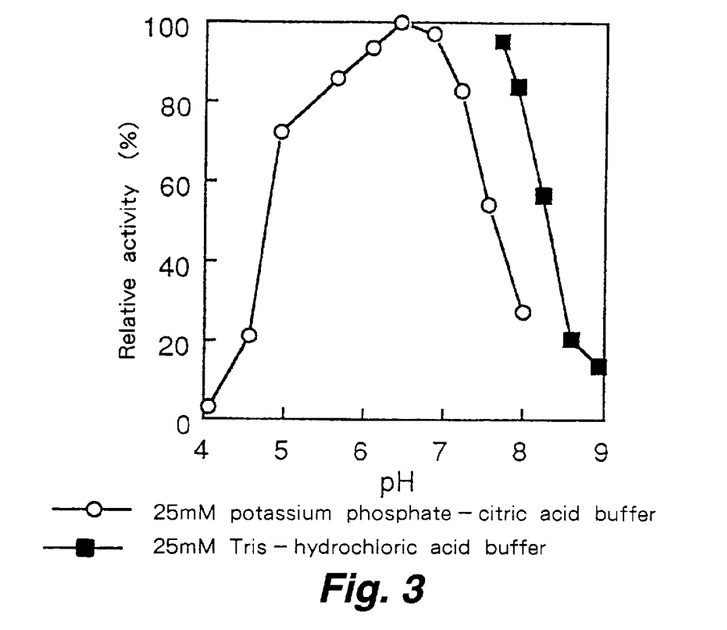
FIG. 3 shows the optimum pH of the heat resistant maltose phosphorylase obtained in the invention.

Reaction was carried out using 25 mM potassium phosphate-citric acid buffer (pH 4.0 to 8.0) or 25 mM Tris-hydrochloric acid buffer (pH 7.5 to 9.0), and as a result, the optimum pH was 6.0 to 7.0 (FIG. 3).

(6) pH stability

Figure 4:
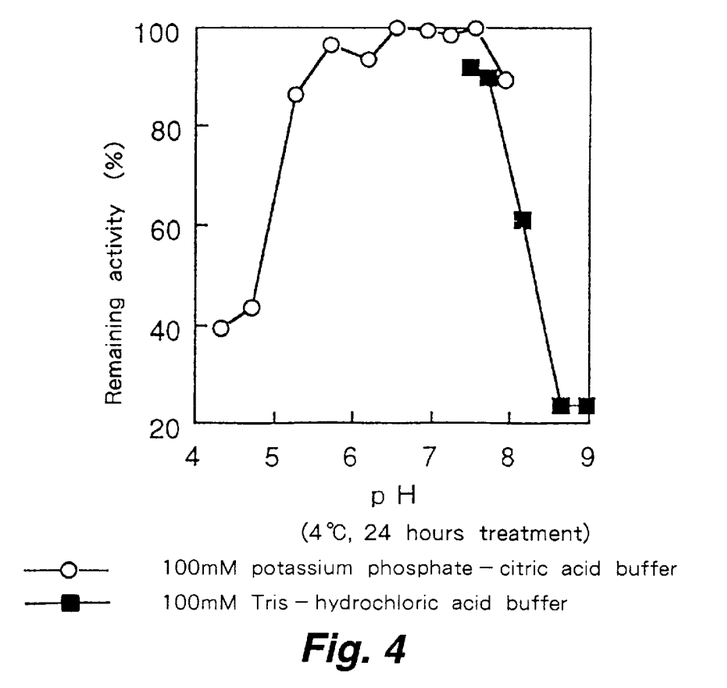
FIG. 4 shows the pH stability of the heat resistant maltose phosphorylase obtained in the invention.

The enzyme was incubated at 4° C. for 24 hours using 100 mM potassium phosphate-citric acid buffer (pH 4.0 to 8.0) or 100 mM Tris-hydrochloric acid buffer (pH 7.5 to 9.0), and the remaining activity at each pH was assayed, and as a result, the enzyme was stable at pH 5.5 to 8.0 (FIG. 4).

(7) Molecular weight

The molecular weight of the enzyme was determined according to gel filtration chromatography using Superdex 200 pg (Pharmacia Biotec Co., Ltd.), from relative elution retention time in comparison with various standard proteins, and as a result, was 150,000 to 190,000.

Its molecular weight determined according to SDS gel electrophoresis, from relative mobility in comparison with various standard proteins was 75,000 to 95,000.

From the results of the gel filtration chromatography and the SDS gel electrophoresis, the enzyme is surmised to form a dimer usually.

(8) Inactivation

100% inactivated when heated at 100° C. for 10 minutes.

(9) Isoelectric point

The enzyme was subjected to isoelectric chromatography using Mono P HR 5/20 column (Pharmacia Biotec Co., Ltd.), and from the pH of the fraction from which the activity was eluted with a developing buffer, the isoelectric point was determined to be 4.7 to 5.1.

(10) Inhibitor

99% inhibition of the activity was observed with 1 mM HgCl$_2$, and 37% inhibition with 1 mM ZnSO$_4$ (Table 2).

Further, the N-terminal amino acid sequence of the purified heat resistant maltose phosphorylase from the above RK-1 strain obtained in Example 1 was determined using a protein sequencer (Protein Sequencer "Model 477A"; Applied Biosystems Co.), and was as follows:

| 1 | 2 | 3 | 4 | 5 | 6 | 7 | 8 | 9 | 10 |
|---|---|---|---|---|---|---|---|---|---|
| Met | Tyr | Tyr | Asn | Arg | Leu | Phe | Asp | Val | Asp |
| 11 | 12 | 13 | 14 | 15 | 16 | 17 | 18 | 19 | 20 |
| Glu | Trp | Thr | Leu | Lys | Thr | Thr | Gln | Leu | His |

The enzymological properties of the heat resistant maltose phosphorylase of the invention and those of so far known maltose phosphorylases originating in microorganisms are shown in comparison in Table 3 and Table 4. As apparent from Table 3 and Table 4, the heat resistant maltose phosphorylase of the invention is different from the known maltose phosphorylases at least in kinds of bacteria as origins, optimum temperature and thermal stability, and thus judged to be novel.

The heat resistant maltose phosphorylase of the invention can be prepared by culturing a microorganism having an ability to produce heat resistant maltose phosphorylase in a nutrient medium, and recovering heat resistant maltose phosphorylase formed from the culture broth.

As to the microorganism to be used for the preparation, any microorganism can be used so long as it is a microorganism belonging to the genus Bacillus and having an ability to produce heat resistant maltose phosphorylase. Specifically, there can be mentioned RK-1 strain separated from soil in Ibaraki Prefecture, and MK-1 strain separated from soil in Chiba Prefecture.

Bacteriological properties of these strains are as shown in Table 5. Both strains were identified to be a bacterium belonging to the genus Bacillus from these properties according to "Bergey's Manual of Systematic Bacteriology" Vol. 2 (1986), but as to species, they do not accord with strains so far reported in properties, and are judged to be novel species. Namely, according to the Bergey's Manual, bacteria of the genus Bacillus which accord with RK-1 strain in culture temperatures at which proliferation is possible are *Bacillus coagulans* and *Bacillus licheniformis*. However, *Bacillus licheniformis* can be judged to be different from RK-1 strain because the former exhibits properties to proliferate at pH 5.7 and 7% NaCl and liquefy gelatin. Further, *Bacillus coagulans* can be judged to be different from RK-1 strain because the former proliferates at pH 5.7 and does not proliferates at 5% NaCl. Further, MK-1 strain according with RK-1 strain in culture temperatures at which proliferation is possible is different from *Bacillus coagulans* and *Bacillus licheniformis* in some of the above points. Both strains are thermophilic bacteria because they can proliferate at a temperature of 55° C., and designated Bacillus sp. RK-1 and Bacillus sp. MK-1, respectively. These RK-1 strain and MK-1 strain were first deposited on Jul. 12, 1995 with National Institute of Bioscience and Human Technology, Agency of Industrial Science and Technology, the Ministry of International Trade and Industry, Japan under the accession numbers of FERM P-15044 and FERM P-15045, respectively, and then transferred there to deposit according to Budapest Treaty on microorganisms on Jul. 17, 1996 and are assigned accession numbers of FERM BP-5592 and FERM BP-5593, respectively.

Microorganisms used in the invention are not limited to wild type strains, and mutants obtained by mutating wild type strains, e.g. the above-mentioned ones according to known artificial mutational means using ultraviolet rays, X-rays, radiations, chemicals (NTG (N-methyl-N⁻-nitro-N-nitrosoguanidine)), EMS (ethyl methanesulfonate), etc.), etc. can also be used so long as they have heat resistant maltose phosphorylase-producing ability.

As to nutrient media used in the invention, any of natural media and synthetic media can be used so long as they contain appropriately carbon sources, nitrogen sources, inorganic matter, and if any, micronutrients necessary for strains used. As carbon sources, there can be used carbohydrates such as maltose, glucose, fructose, sucrose, starches, dextrin and glycerol, etc. As nitrogen sources, there can be used inorganic and organic nitrogen compounds such as ammonium chloride, ammonium sulfate, urea, ammonium nitrate, sodium nitrate, amino adids (glutamic acid, etc.) and uric acid.

As nitrogen sources, there can also be used nitrogen-containing natural products such as peptone, polypeptone, meat extract, yeast extract, corn steep liquor, soybean meal, soybean cake, dry yeast, Casamino acid and soluble vegetable protein.

As inorganic matter, there can be used potassium dihydrogenphosphate, dipotassium hydrogenphosphate, magnesium sulfate, ferrous sulfate, manganese sulfate, zinc sulfate, sodium chloride, potassium chloride, calcium chloride, etc. In addition, micronutrients such as biotin and thiamine are used if necessary.

In the invention, although it is possible to produce heat resistant maltose phosphorylase without making maltose exist in the medium as a maltose phosphorylase-inducing substance, there is a case where the amount of heat resistant maltose phosphorylase formed can be increased by the presence of maltose.

As culture methods, liquid culture methods (shaking culture methods or aeration stirring culture methods) are preferred, and industrially, aeration stirring culture methods are particularly preferred. Culture temperature can be in the range of 30° to 60° C., but is preferably 50° to 55° C. Culture pH is preferably 6.5 to 7.5. Culture time varies depending on culture conditions, but is usually on the order of 15 to 48 hours, and when formation of heat resistant maltose phosphorylase was confirmed, preferably when the formation reached a maximum, the culture is ceased.

For recovering the heat resistant maltose phosphorylase of the invention from the thus obtained culture broth, the culture broth is first fractionated into the culture liquid fraction and the cell fraction by centrifugation methods or filtration methods. The heat resistant maltose phosphorylase is detected in both of the above fractions, but mainly obtained from the culture liquid fraction, and therefore, this fraction is further subjected to one or any combination of well-known isolation or purification methods such as ultrafiltration, salting-out, dialysis, solvent precipitation, ion exchange chromatography, hydrophobic chromatography, adsorption chromatography and isoelectric chromatography, whereby concentrated or purified preparations of heat resistant maltose phosphorylase can be obtained. A specific example of isolation or purification of the heat resistant maltose phosphorylase of the invention is shown in Example 1.

This invention also relates to a process for preparation of β-glucose-1-phosphoric acid which comprises reacting maltose with phosphoric acid or a phosphate salt in an aqueous medium, at 55° to 70° C., at pH 4.5 to 8.0, in the presence of heat resistant maltose phosphorylase having an activity of 80% or more of the one untreated after treated in a buffer of pH 6.0, at one temperature of 50° to 60° C. for 15 minutes.

As heat resistant maltose phosphorylase used in this case, there can preferably be used one having an activity of 80% or more of the one untreated after treated in a buffer of pH 6.0, e.g. 10 mM potassium phosphate-citric acid buffer (pH 6.0), at one temperature of 50° to 60° C., preferably at one temperature of 55 to 60° C., particularly preferably at 60° C., for 15 minutes. Specifically, there can be mentioned an enzyme having properties of at least (1) to (6) or at least (1) to (7) among the enzymological properties of the above (1) to (10). These enzymes can either be purified enzymes or crude enzymes containing other enzymes having no bad influence on the above method for preparation of β-glucose-1-phosphoric acid. As the crude enzymes, there can be mentioned a crude enzyme obtained by precipitating heat resistant maltose phosphorylase from a fraction containing the enzyme such as the above culture liquid fraction by salting-out or solvent precipitation, or a crude enzyme in a middle step of purification obtained by further purifying the above crude enzyme by the above-mentioned purification means. It is further possible to use an immobilized enzyme obtained by immobilizing such an enzyme on a carrier by a usual method.

As maltose, there can be used maltose or maltose-containing matter (e.g., sugar solutions containing maltose in high concentrations). As the phosphate salt, there can be used water-soluble phosphate salts such as tripotassium (or trisodium) phosphate, dipotassium (or disodium) hydrogenphosphate and potassium (or sodium) dihydrogenphosphate. As the aqueous medium, there can be mentioned water, buffers, etc. As the buffers, there can be used acetate buffers, potassium phosphate-citric acid buffers, citrate buffers, succinate buffers, Tris-hydrochloric acid buffers, etc.

As to the use amount of the enzyme, there is no particular limitation, but it is suitable to use it in an amount of 0.1 to 50 units, preferably 1 to 20 units per g of maltose. Although there is no particular limitation, it is suitable to use phosphoric acid and/or the phosphate salt in an amount of 0.1 to 10 times, preferably 0.5 to 2 times the molar amount of maltose. In this connection, when the buffer is a buffer containing phosphoric acid (or a phosphate salt), e.g. a potassium phosphate-citric acid buffer, it is sufficient if the total amount of phosphoric acid and the phosphate salt is in the above range.

For avoiding contamination with various germs and increasing the yield, the above reaction is carried out at 55° to 70° C., preferably 55° to 65° C., more preferably 60° to 65° C. It is suitable that the pH is generally 4.5 to 8.0, preferably 5.0 to 6.0. More specifically, it is further preferred for prevention of contamination with various germs to carry out the reaction at pH 4.5 to 5.0 in the case of the temperature of 55° to 60° C., at pH 5.0 to 5.5 in the case of the temperature of 60° to 65° C., and at pH 5.5 to 6.5 in the case of the temperature of 65° to 70° C. The reaction is ceased at the time when sufficient formation of β-glucose-1-phosphoric acid is observed under the above conditions, but the reaction is usually ceased in 1 to 144 hours.

After completion of the reaction, the reaction is ceased by a suitable means such as inactivation of the enzyme with heating of the reaction solution or inactivation of the enzyme with lowering of the pH (addition of an acid such as hydrochloric acid), and isolation and purification methods such as active carbon treatment and ion exchange resin treatment are applied in an appropriate combination to obtain β-glucose-1-phosphoric acid.

This invention also relates to a process for preparation of trehalose which comprises reacting maltose with phosphoric acid or a phosphate salt in an aqueous medium, at 55° to 70° C., at pH 4.5 to 8.0, in the presence of heat resistant maltose phosphorylase having an activity of 80% or more of the one untreated after treated in a buffer of pH 6.0, at one temperature of 50° to 60° C. for 15 minutes, and heat resistant trehalose phosphorylase.

As the heat resistant maltose phosphorylase in the above process, there can be used the same ones as in the above process for preparation of β-glucose-1-phosphoric acid can be used. As the heat resistant trehalose phosphorylase, any one can be used so long as it can produce trehalose from maltose and phosphoric acid or a phosphate salt at one of the above reaction temperatures and at one of the above pH values, with the aid of the heat resistant maltose phosphorylase. However, there can, preferably, be used heat resistant trehalose phosphorylase having an activity of 95% or more of the one untreated after treated in a buffer of pH 6.0, at one temperature of 50° to 65° C., preferably at one temperature of 55° to 65° C., further preferably at one temperature of 60° to 65° C., particularly preferably at 65° C., for 15 minutes. As an example of heat resistant trehalose phosphorylase having such a property, there can be mentioned heat resistant trehalose phosphorylase which *Bacillus stearothermophilus* SK-1 found by the present inventors produces. The SK-1 strain was first deposited on Sep. 29, 1994 with National Institute of Bioscience and Human Technology, Agency of Industrial Science and Technology, the Ministry of International Trade and Industry, Japan under an accession number of FERM P-14567, and then transferred there to deposit according to Budapest Treaty on microorganisms on Jul. 17, 1996, and is assigned an accession number of FERM BP-5594. An example of preparation of the above heat resistant trehalose phosphorylase is shown in Example 4 (crude enzyme) and Reference example 1 (purified enzyme). The enzymological properties of this purified enzyme are as follows.

(1) Action

Phosphorolyze trehalose reversibly, as shown in Formula (2). Namely, when it is made to act on trehalose in the presence of phosphoric acid, it produces glucose and β-glucose-1-phosphoric acid in an equimolar amount, and when it is made to act on glucose and β-glucose-1-phosphoric acid, it produces trehalose and phosphoric acid in an equimolar amount.

*trehalose+phosphoric acid⇌glucose+β-glucose-1-phosphoric ac(2)*

(2) Substrate specificity

Phosphorolysis reaction was carried out using trehalose, neotrehalose, maltose, isomaltose, cellobiose, sucrose, p-nitrophenyl-α-D-glucoside and p-nitrophenyl-β-D-glucoside as substrates, and as a result, formation of glucose was scarcely observed except trehalose (Table 6).

(3) Optimum temperature

Figure 6:
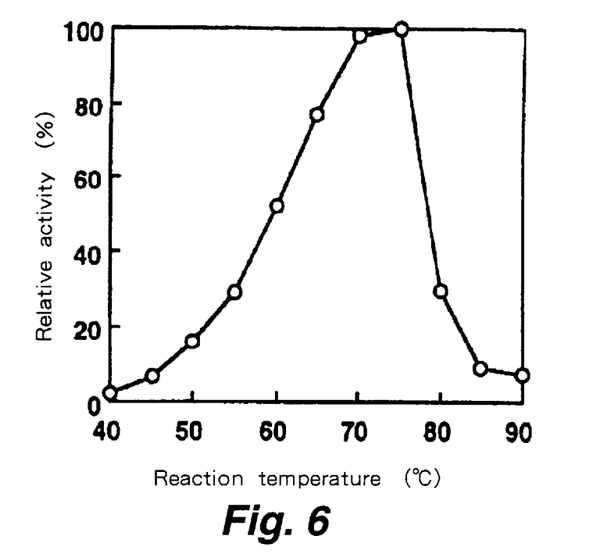
FIG. 6 shows the optimum temperature of a heat resistant trehalose phosphorylase which was obtained from *Bacillus stearothermophilus* SK -1 and can be used for preparation of trehalose through reaction of maltose with phosphoric acid or a phosphate salt.

Reaction was carried out in 40 mM potassium phosphate-citric acid buffer (pH 6.0) at various temperatures (40° to 90° C.), and as a result, the optimum temperature of trehalose phosphorolysis reaction was from around 70° C. to around 75° C., and the enzyme exhibited about 50% or more of the maximum activity in the range of 60° C. to 75° C. (FIG. 6).

(4) Thermal stability

Figure 7:
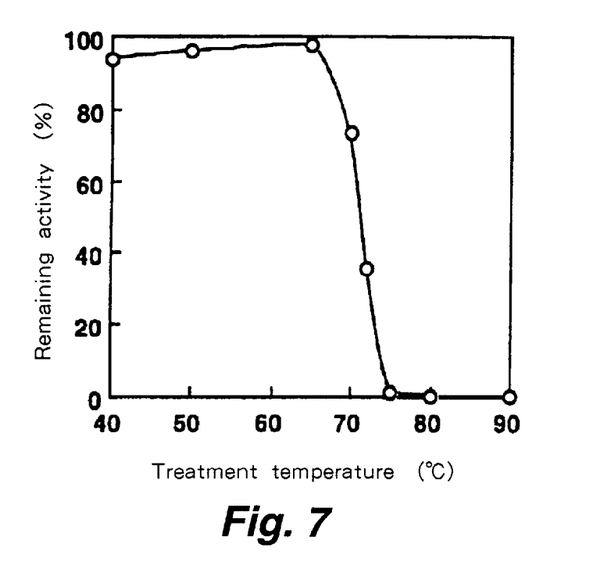
FIG. 7 shows the thermal stability of the heat resistant trehalose phosphorylase obtained from *Bacillus stearothermophilus* SK-1.

The enzyme was incubated in 10 mM potassium phosphate-citric acid buffer (pH 6.0) and the remaining activity was assayed, and as a result, it exhibited an activity of 95% or more of the one untreated after treatment at 65° C. for 15 minutes (FIG. 7).

(5) Optimum pH

Figure 8:
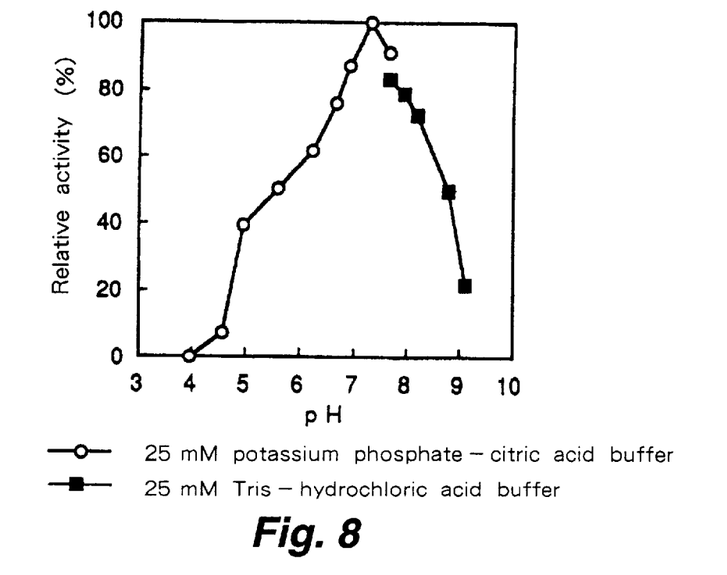
FIG. 8 shows the optimum pH of the heat resistant trehalose phosphorylase obtained from *Bacillus stearothermophilus* SK -1.

Reaction was carried out at 60° C. using 25 mM potassium phosphate-citric acid buffer (pH 4.0 to 7.7) or 25 mM Tris-hydrochloric acid buffer (pH 7.7 to 9.0), and as a result, the optimum pH was 6.5 to 7.5 (FIG. 8).

(6) pH stability

Figure 9:
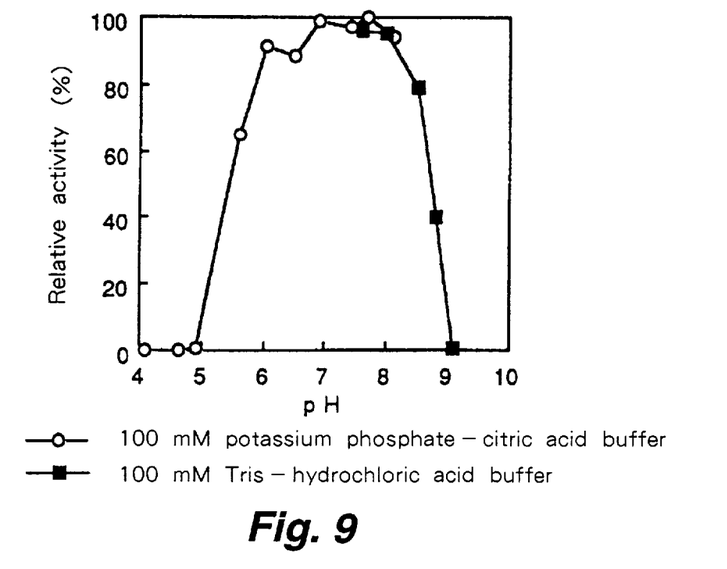
FIG. 9 shows the pH stability of the heat resistant trehalose phosphorylase obtained from *Bacillus stearothermophilus* SK -1.

The enzyme was incubated at 60° C. for 24 hours using 100 mM potassium phosphate-citric acid buffer (pH 4.0 to 8.0) or 100 mM Tris-hydrochloric acid buffer (pH 7.5 to 9.0), and the remaining activity at each pH was assayed, and as a result, the enzyme was stable at pH 6.0 to 8.0 (FIG. 9).

(7) Molecular weight

The molecular weight of the enzyme was determined according to gel filtration chromatography using Superdex 200 pg (Pharmacia Biotec Co., Ltd.), from relative elution retention time in comparison with various standard proteins, and as a result, was 110,000 to 150,000.

(8) Inactivation

100% inactivated when heated at 100° C. for 10 minutes.

(9) Isoelectric point

The enzyme was subjected to isoelectric focusing, and its isoelectric point was determined to be 4.6 to 5.2 from the relative mobilities to various standard proteins.

(10) Inhibitor

99% inhibition of the activity was observed with 1 mM $HgCl_2$, and 80% inhibition with 1 mM $ZnSO_4$ (Table 7).

The heat resistant trehalose phosphorylase can be purified ones or crude ones, as in the case of the heat resistant maltose phosphorylase, and these purified enzymes and crude enzymes can be obtained, as in the case of the heat resistant maltose phosphorylase.

As the maltose, phosphoric acid, phosphate salt and aqueous medium, there can be used the same ones as in the above process for preparation of β-glucose-1-phosphoric.

As to the use amount of the enzyme, there is no particular limitation, but it is suitable to use each enzyme in an amount of 0.1 to 50 units, preferably 1 to 20 units per g of maltose. Further, although there is no particular limitation on the use rate between the heat resistant maltose phosphorylase and the heat resistant trehalose phosphorylase, it is suitable that the rate is the former: the latter=1:5 to 5:1, preferably 1:2 to 2:1, as the ratio of unit.

In this connection, trehalose phosphorylase activity was assayed by the following method. An enzyme solution (0.4 ml), 0.06 ml of 0.5M potassium phosphate-citric acid buffer (pH 6.0), 0.6 ml of 2 w/v % trehalose and 0.14 ml of distilled water were mixed, and reaction was carried out at 60° C. for 20 minutes and ceased by boiling for 10 minutes. Then, 0.02 ml of a sample was taken from the reaction-ceased solution, 3 ml of a reagent for glucose examination (Glucose CII-Test Wako; Wako Pure Chemical Industries, Ltd.) was added, reaction was carried out at room temperature for 20 minutes, the absorbance at 505 nm was measured using a spectrophotometer, and the amount of glucose formed in the reaction solution was determined from the measured value. As to the definition of the trehalose phosphorylase activity, the amount of the enzyme necessitated to phosphorolyze 1 μmol of trehalose in one minute under the above assay conditions was assumed to be 1 unit.

Reactions can be carried out by simultaneously adding the heat resistant maltose phosphorylase and the heat resistant trehalose phosphorylase to maltose, or by first making the heat resistant maltose phosphorylase act on maltose and then adding the heat resistant trehalose phosphorylase. When the heat resistant trehalose phosphorylase is added afterward, there is no particular limitation on the time of addition, but it is preferred to make the addition by the time when formation of β-glucose-1-phosphoric acid becomes a maximum.

Although there is no particular limitation, it is suitable to use phosphoric acid or a phosphate salt in an amount of 0.001 to 1 times, preferably 0.005 to 0.5 times the molar amount of maltose. The reaction temperature, reaction pH and reaction time can be the same as in preparation of β-glucose-1-phosphoric acid. The isolation and purification of trehalose after completion of the reaction can be carried out by an appropriate combination of means such as active carbon treatment, ion exchange treatment and ethanol crystallization treatment.

The invention is further detailedly described below according to examples.

EXAMPLE 1

Preparation and purification of heat resistant maltose phosphorylase by Bacillus sp. RK-1 (FERM BP-5592) were carried out as follows.

(Culture)

A medium (pH 7.0) (100 ml) containing 1 w/v % yeast extract, 2 w/v % polypeptone and 1 w/v % maltose was put in a 500-ml Meyer flask with baffles, and autoclave sterilized at 121° C. for 20 minutes. One loopful of Bacillus sp. RK-1 was inoculated into the resultant medium, and shaking cultured at 55° C. for 16 hours to give a seed culture.

A medium (about 3 L) having the same composition as in the seed culture was put in a 5-L fermentor, sterilized and warmed to a temperature of 55° C. The seed culture was inoculated in a ratio of 2 v/v %, and cultured with aeration and stirring for 18 hours while the temperature and pH were maintained 55° C. and 6.0 to 7.0, respectively.

(Preparation of crude enzyme)

After completion of the culture, the culture broth was centrifuged to remove the cells, ammonium sulfate was dissolved in the supernatant so as to be 40 to 60% saturation. The resultant protein precipitate was recovered by centrifugation, and dissolved in 10 mM acetate buffer (pH 6.0), and the solution was dialyzed against the same buffer and then concentrated to give 20 ml of a crude enzyme solution of about 300 units /ml.

(Ion exchange chromatography)

The crude enzyme solution was added to a column packed with TSKgel DEAE TOYO Pearl 650M (TOSOH CORPORATION) and equilibrated with 10 mM acetate buffer (pH 6.0), elution was carried out by ascending concentration gradient of 0 to 0.5M NaCl, and the eluate was taken in portions. Active fractions were combined, concentrated and desalted using an ultrafiltration membrane, and further subjected to a series of the same chromatography operations to heighten the purification degree.

(Gel filtration chromatography)

The resultant partially purified enzyme solution was added to a Superdex 200 pg column (Pharmacia Biotec Co., Ltd.) equilibrated with 10 mM acetate buffer (pH 6.0) dissolving 0.2M NaCl, elution was carried out with the same buffer, and the eluate was taken in portions. Active fractions were concentrated and desalted using an ultrafiltration membrane.

(Isoelectric chromatography)

The resultant partially purified enzyme solution was added to a Mono P HR 5/20 column (Pharmacia Biotec Co., Ltd.) equilibrated with 25 mM bisTris-hydrochloric acid buffer (pH 7.1), elution was carried out with a developing buffer (Polybuffer; Pharmacia Biotec Co., Ltd.) adjusted to pH 4.0, and the eluate was taken in portions. Active fractions were concentrated and desalted using an ultrafiltration membrane.

(Native polyacrylamide gel electrophoresis)

The resultant purifed enzyme solution was native polyacrylamide gel electrophoresed, the resultant gel was stained with CBB (Coomassie Brilliant Blue) and checked on bands of proteins. As a result, only one band was detected, and thus the enzyme was confirmed to be a single protein.

(Confirmation of maltose phosphorylase)

The above purifed enzyme solution (0.4 ml) was mixed with 0.06 ml of 0.5M potassium phosphate-citric acid buffer (pH 6.0), 0.6 ml of 2 w/v % maltose and 0.14 ml of distilled water, and reaction was carried out at 60° C. for 15 minutes and ceased by boiling of 10 minutes.

Then, 0.02 ml of a sample was taken from the reaction-ceased solution, 3 ml of a reagent for glucose examination (Glucose CII-Test Wako; Wako Pure Chemical Industries, Ltd.) was added, reaction was carried at room temperature for 20 minutes, the absorbance at 505 nm was measured using a spectrophotometer, and the amount of glucose formed in the reaction solution was determined from the measured value.

Further, part of the reaction-ceased solution was separated by high performance liquid chromatography using an anion exchane column (TSKgel SAX (150×6.0 mm φ; TOSOH CORPORATION), eluent 0.1M aqueous potassium acetate solution (pH 5.0), flow rate 1.0 ml/min, column temperature 30° C.), and then β-glucose-1-phosphoric acid was detected and quantatively determined by a differential refractometer (Shodex; Showa Denko Co., Ltd.). As a result, the glucose content and the β-glucose-1-phosphoric content in the reaction-ceased solution are the same, whereby it was confirmed that the purifed enzyme was maltose phosphorylase.

EXAMPLE 2

Preparation of heat resistant maltose phosphorylase by Bacillus sp. MK-1 (FERM BP-5593) was carried out as follows.

A medium (pH 7.0) (100 ml) containing 1 w/v % yeast extract, 2 w/v % polypeptone and 1 w/v % maltose was put in a 500-ml Meyer flask with baffles, and autoclave sterilized at 121° C. for 20 minutes. One loopful of Bacillus sp. MK-1 was inoculated into the resultant medium, and shaking cultured at 55° C. for 16 hours to give a seed culture. A medium (about 3 L) having the same composition as in the seed culture was put in a 5-L fermentor, sterilized and warmed to a temperature of 55° C. The seed culture was inoculated in a ratio of 2 v/v %, and cultured with aeration and stirring for 48 hours while the temperature and pH were maintained 55° C. and 6.0 to 7.0, respectively.

After completion of the culture, the culture broth was centrifuged to separate the cells. These cells were washed, suspended in a 10 mM acetate buffer and ruptured by ultrasonic treatment, and the solid matter was removed by centrifugation to give 20 ml of a crude enzyme solution. This crude enzyme solution had a maltose phosphorylase activity of about 10 units/ml.

EXAMPLE 3

An attempt was carried out to make the heat resistant maltose phosphorylase crude enzyme slution (that at the stage of ammonium sulfate fractionation) prepared in Example 1 act on maltose as a substrate to produce β-glucose-1-phosphoric acid.

A solution for reaction of 30 w/v % maltose, 10 u/g the enzyme and 0.5M phosphoric acid (pH 6.0) was prepared by adjustment with 1M potassium phosphate buffer (pH 6.0), and reaction was carried out at 60° C. for 4 hours. Discontinuation of the reaction was carried out by heating at 100° C. for 10 minutes. After completion of the reaction, part of the reaction solution was separated by high performance liquid chromatography using an anion exchane column (TSKgel SAX (150×6.0 mm φ; TOSOH CORPORATION), eluent 0.1M aqueous potassium acetate solution (pH 5.0), flow rate 1.0 ml/min, column temperature 30° C.), and then β-glucose-1-phosphoric acid was quantatively determined by a differential refractometer (Shodex ; Showa Denko Co., Ltd.). As a result, β-glucose-1-phosphoric acid was produced at a concentration of 4.6 w/v %.

The residual reaction solution was separated by chromatography under the conditions of ion exchane column: TSKgel SAX (200×55 mm φ) (TOSOH CORPORATION), eluent: 0.1M aqueous potassium acetate solution (pH 5.0) and flow rate: 10.0 ml/min, and fractions of β-glucose-1-phosphoric acid were taken. The fraction solution was adjusted to pH 8.5 with 20% NaOH, 2 volumes of ethanol was added, the resultant mixture was left alone at 0° to 4° C. for 24 hours, and disodium β-glucose-1-phosphate precipitated was recovered by centrifugation. As a result, disodium β-glucose-1-phosphate having a purity of 95% or more was obtained in a yield of 90%.

EXAMPLE 4

(Preparation of heat resistant trehalose phosphorylase)

A medium (pH 7.0) (100 ml) containing 0.12 w/v % meat extract, 0.4 w/v % polypeptone and 0.2 w/v % NaCl was put in a 500-ml Meyer flask with baffles, and autoclave sterilized at 121° C. for 20 minutes. One loopful of Bacillus stearothermophilus SK-1 (FERM BP-5594) was inoculated into the resultant medium, and shaking cultured at 55° C. for 16 hours to give a seed culture.

A medium (pH 7.0) (about 3 L) containing 1 w/v % yeast extract, 2 w/v % polypeptone and 1 w/v % trehalose was put in a 5-L fermentor, sterilized and warmed to a temperature of 55° C. The seed culture was inoculated in a ratio of 2 v/v %, and cultured with aeration and stirring for 40 hours while the temperature and pH were maintained 55° C. and 6.0 to 7.0, respectively.

After completion of the culture, the culture broth was centrifuged to remove the cells, ammonium sulfate was dissolved in the supernatant so as to be 80% saturation. The resultant protein precipitate was recovered by centrifugation, and dissolved in 10 mM acetate buffer (pH 6.0), and the solution was dialyzed against the same buffer and then concentrated to give 20 ml of a crude enzyme solution having a trehalose phosphorylase activity of about 220 units/ml.

(Reaction of formation of trehalose from maltose)

The thus prepared heat resistant trehalose phosphorylase crude enzyme solution and the heat resistant maltose phosphorylase crude enzyme solution (that at the stage of ammonium sulfate fractionation) prepared in Example 1 were made to act on maltose as a substrate to convert it to trehalose.

Namely, enzymatic reaction was carried out under the conditions of maltose concentration (20 or 30 w/v %), phosphoric acid concentration (5 to 300 mM), each enzyme amount (1 to 10 units/ml) (each enzyme was used in the same unit amount), temperature, pH and time shown in Table 6. In this connection, pH adjustment was carried out with an acetate buffer.

Discontinuation of the reaction was carried out by heating at 100° C. for 10 minutes. After completion of the reaction, each reaction solution was subjected to high performance liquid chromatography using as detecting means TSKgel Amido 80 column (TOSOH CORPORATION), eluent: acetonitrile/water (76/24), flow rate: 0.8 ml/min, column temperature : 80° C., and differential refractometer: Shodex (Showa Denko Co., Ltd.), and thereby the sugar composition of each reaction solution was quantitatively determined.

Further, β-glucose-1-phosphoric acid was quantitatively determined by subjecting the reaction solution to high performance liquid chromatography using the same anion exchange column as in Example 1. The results are shown in Table 8.

Maltose was converted to trehalose at yields of 18 to 65% under the reaction conditions of the reaction temperature of 60° to 70° C. and pH 5.0 to 6.0.

EXAMPLE 5

Preparation of trehalose-containing sugar solution, and trehalose-highly containing sugar solution and powder thereof)

A branch-cutting enzyme (sold by Amano Seiyaku Co., Ltd./Pullulanase "Amano") and β-amylase (sold by NAGASE & CO., LTD./β-amylase) were made to act on a starch-liquefied solution obtained by making α-amylase act on corn starch, and thereby a maltose-highly containing sugar solution (solid content 30 w/w %, maltose purity per the solid components 80%) was prepared. The heat resistant maltose phosphorylase crude enzyme solution (that at the stage of ammonium sulfate fractionation) prepared in Example 1 using Bacillus sp. RK-1 and the heat resistant trehalose phosphorylase crude enzyme solution prepared in Example 4 using *Bacillus stearothermophilus* SK-1 were added thereto so that the amounts of the enzymes added became 10 units per g of the solid components, respectively. Further, potassium phosphate was added thereto so that the phosphoric acid concentration became 10 mM, reaction was carried out at 60° C. and pH 5.0 for 72 hours, and the resultant solution was heated at 100° C. for 10 minutes to inactivate the enzymes.

Figure 5:
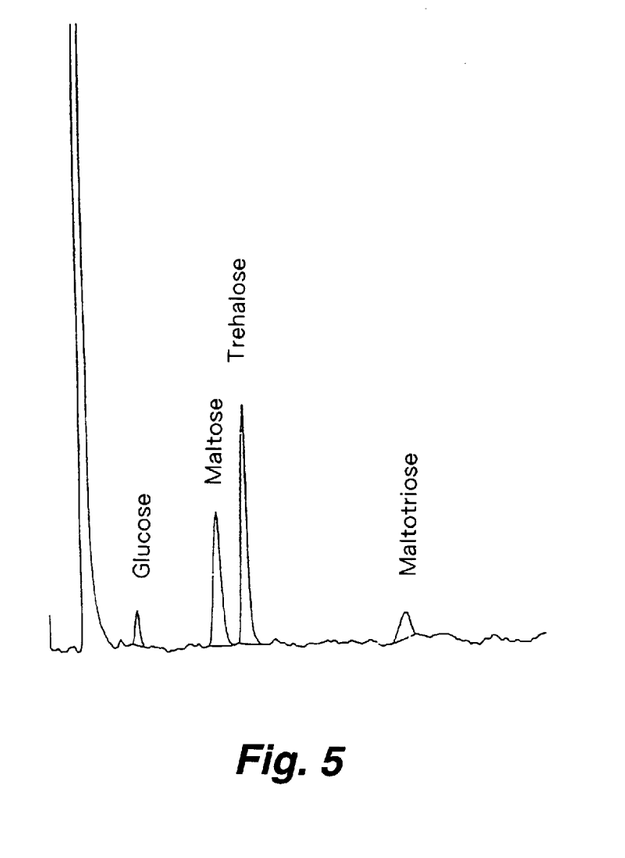
FIG. 5 shows a chart obtained by analyzing, by high performance liquid chromatography, a trehalose-containing sugar solution obtained by making the heat resistant maltose phosphorylase of the invention and a heat resistant trehalose phosphorylase act on a maltose-highly containing sugar solution (Example 5).

The resultant reaction solution was decolorized with active carbon, desalted with an ion exchange resin, and concentrated to a concentration of about 70% to give a trehalose-containing sugar sulution. This sugar solution was analyzed by high performance liquid chromatography as in Example 4, and the resultant chart is shown in FIG. 5. The rates (w/w) per the solid components were glucose 1.5%, trehalose 64.5%, maltose 18.0%, maltotriose 11.2% and other maltooligosaccharides 4.8%.

Further, glucoamylase (sold by Seikagaku Kogyo Co., Ltd., gluco amylase) was added to the above reaction solution so that the amount became 1 unit per g of the solid components, and the mixture was subjected to reaction at 55° C. for 8 hours and then heated at 100° C. for 10 minutes to inactivate the enzyme. The resultant reaction solution was decolorized with active carbon, desalted with an ion exchange resin, concentrated to a concentration of about 50%, and subjected to separation with a sodium type ion exchange column, and the eluate was taken in portions. The trehalose fractions were taken and concentrated to give a trehalose-highly containing sugar solution having a solid content of 70% and containing trehalose at a rate of 92% per the solid components.

Further, powder trehalose could be obtained by concentrating and then drying this trehalose-highly containing sugar solution.

REFERENCE EXAMPLE 1

Preparation and purification of heat resistant trehalose phosphorylase by *Bacillus stearothermophilus* SK-1 (FERM BP-5594) were carried out as follows.

(Culture)

One loopful of the SK-1 strain was inoculated into a liquid medium (pH 7.0) containing 0.5 w/v % yeast extract, 2 w/v % polypeptone and 1 w/v % maltose and autoclave sterilized at 121° C. for 20 minutes, and cultured with aeration and shaking at 55° C. for 72 hours. Then, the resultant culture broth was separated into the cells and the culture solution by centrifugation.

(Preparation of crude enzyme)

Ammonium sulfate was dissolved in the culture solution so as to be 40 to 60% saturation, the resultant protein precipitate was recovered by centrifugation and dissolved in 10 mM potassium phosphate-citric acid buffer (pH 6.0), and the solution was dialyzed against the same buffer to give a crude enzyme solution.

(Ion exchange chromatography)

The crude enzyme solution was added to a column packed with TSKgel DEAE TOYO Pearl 650M (TOSOH CORPORATION) and equilibrated with 10 mM potassium phosphate-citric acid buffer (pH 6.0), elution was carried out by ascending concentration gradient using 5 column volumes of 0 to 0.4M NaCl, and the eluate was taken in portions. Active fractions were combined, and concentrated and desalted using an ultrafiltration membrane, and then further subjected to a series of the same chromatography operations to heighten the purification degree.

(Hydrophobic chromatography)

The resultant partially purified enzyme solution was added to a column packed with TSKgel Phenyl TOYO Pearl 650M (TOSOH CORPORATION) and equilibrated with 10 mM potassium phosphate-citric acid buffer (pH 6.0) dissolving ammonium sulfate so as to be 40% saturation, elution was carried out by descending concentration gradient using 8 column volumes of 40 to 0% saturated ammonium sulfate solutions, and the eluate was taken in portions. Active fractions were combined, and concentrated and desalted using an ultrafiltration membrane.

(Adsorption chromatography)

The resultant partially purified enzyme solution was added to a PENTAX GH-0810M (Asahi Optical Co., Ltd.) column equilibrated with 10 mM potassium phosphate-citric acid buffer (pH 6.0) dissolving $CaCl_2$ so as to be 0.3 mM, elution was carried out by ascending concentration gradient using 10 column volumes of 10 to 300 mM potassium phosphate-citric acid buffer (pH 6.0), and the eluate was taken in portions. Active fractions were combined, and concentrated and desalted using an ultrafiltration membrane.

(Gel filtration chromatography)

The resultant partially purified enzyme solution was added to a column packed with Superdex 200 pg (Pharmacia Biotec Co., Ltd.) and equilibrated with 10 mM potassium phosphate-citric acid buffer (pH 6.0) dissolving NaCl so as to be 0.2M, elution was carried out using the same buffer, and the eluate was taken in portions. Active fractions were combined, and concentrated and desalted using an ultrafiltration membrane.

(Native polyacrylamide gel electrophoresis)

The resultant purifed enzyme solution was native polyacrylamide gel electrophoresed, the resultant gel was stained with CBB and checked on bands of proteins. As a result, only one band was detected, and thus the enzyme was confirmed to be a single protein.

As described above, maltose phosphorylase provided by the invention has heat resistance, and produces β-glucose-1-phosphoric from maltose and phosphoric acid. By using this enzyme, or this enzyme and trehalose phosphorylase, it is possible to prepare β-glucose-1-phosphoric acid or trehalose, respectively, industrially advantageously, with lowering of contamination with various germs and shortening of reaction time.

TABLE 1

| Substrate specificity (Heat resistant maltose phosphorylase) | |
|---|---|
| Substrate | Relative activity (%) |
| Maltose | 100 |
| Isomaltose | 2 |
| Trehalose | 0 |
| Neotrehalose | 0 |
| Cellobiose | 0 |
| Gentiobiose | 2 |
| Soluble starch | 2 |
| Sucrose | 0 |
| Lactose | 0 |
| p - Nitrophenyl - α - D - glucoside | 0 |
| p - Nitrophenyl - β - D - glucoside | 0 |

TABLE 2

| Inhibitor (Heat resistant maltose phosphorylase) | |
|---|---|
| Inhibitor* | Relative activity (%) |
| $FeCl_2$ | 94 |
| $MgCl_2$ | 100 |
| $MnSO_4$ | 111 |
| $CaCl_2$ | 101 |
| Pb $(CH_3COO)_2$ | 99 |
| Ba $(OH)_2$ | 100 |
| $ZnSO_4$ | 63 |
| $CuSO_4$ | 91 |
| $HgCl_2$ | 1 |
| EDTA.2Na | 100 |
| β - Mercaptoethanol | 94 |
| DTT** | 101 |
| PCMB*** | 20 |
| No addition | 100 |

*1 mM
**Dithiothreitol
***p - (Chloromercuri) benzoic acid

TABLE 3

Comparison among maltose phosphorylases

|  | Maltose phosphorylase of the invention | Maltose phosphorylase of Agr. Biol. Chem. 37, 2813–2819, 1973 | Maltose phosphorylase of Japanese Published Unexamined Patent Application No. 91778/1989 | Maltose phosphorylase of Nippon Nogei Kagaku Kaishi, 69 (extraordinary extra number), 28, 1995 |
|---|---|---|---|---|
| Kind of bacterium | Bacillus sp. | *Lactobacillus brevis* | *Lactobacillus sanfrancisco* | Plesiomonas |
| Enzymatic reaction | Maltose + phosphoric acid ⇌ glucose + β GIP* | Maltose + phosphoric acid ⇌ glucose + β GIP* | Maltose + phosphoric acid ⇌ glucose + β GIP* | Maltose + phosphoric acid ⇌ glucose + β GIP* |
| Optimum temperature of enzymatic reaction | 55~70° C. | Not disclosed | 40~45° C. | 50° C. |
| Thermal stability of enzyme | Not inactivated at 55° C. in 15 minutes or less | Not inactivated at 40° C. in 10 minutes or less | Not inactivated at 40° C. in 15 minutes or less | Stable at 40° C. or less |
| Optimum pH of enzymatic reaction | 6.0~7.0 | 6.5 | 5.5 | 7.5~8.0 |
| pH stability of enzyme | Stable in the range of pH 5.5~8.0 | Stable in the range of pH 5.0~8.0 | Stable in the range of pH 6.0~7.0 | Stable in the range of pH 5.5~7.0 |
| Molecular weight | 150,000~190,000 | 150,000 | 150,000 | 200,000 |
| Isoelectric point | 4.7~5.1 | Not disclosed | Not disclosed | 3.8 |

*β-Glucose-1-phosphoric acid

TABLE 4

Comparison among maltose phosphorylase

|  | Maltose phosphorylase of Japanese Published Examined Patent Application No. 54036/1985 | Maltose phosphorylase of Japanese Published Examined Patent Application No. 54036/1985 | Maltose phosphorylase of Japanese Published Examined Patent Application No. 54036/1985 | Maltose phosphorylase of Oyo Toshitsu Kagaku, 42 (1), 19–25, 1995 |
|---|---|---|---|---|
| Kind of bacterium | *Lactobacillus plantarum* | *Lactobacillus reuteri* | *Lactobacillus fermentum* | Plesiomonas |
| Enzymatic reaction | Maltose + phosphoric acid ⇌ glucose + β GIP* | Maltose + phosphoric acid ⇌ glucose + β GIP* | Maltose + phosphoric acid ⇌ glucose + β GIP* | Maltose + phosphoric acid ⇌ glucose + β GIP* |
| Optimum temperature of enzymatic reaction | Not disclosed | Not disclosed | Not disclosed | Not disclosed |
| Thermal stability of enzyme | Not disclosed | Not disclosed | Not disclosed | Not disclosed |
| Optimum pH of enzymatic reaction | Not disclosed | Not disclosed | Not disclosed | Not disclosed |
| pH stability of enzyme | Not disclosed | Not disclosed | Not disclosed | Not disclosed |
| Molecular weight | Not disclosed | Not disclosed | Not disclosed | Not disclosed |
| Isoelectric point | Not disclosed | Not disclosed | Not disclosed | Not disclosed |

*β-Glucose-1-phosphoric acid

TABLE 5

Microbiological characteristics of RK - 1 strain and MK - 1 strain

|  | Test result | |
|---|---|---|
| Test item | RK - 1 | MK - 1 |
| Form | *bacillus* | *bacillus* |
| Gram staining | + | + |
| Endospore | + | + |
| Shape | ellipsoidal | ellipsoidal |
| Position | terminal ~ | terminal ~ |
| Sporangium | subterminal swollen | subterminal swollen |
| Mobility | + | + |
| Attitude to oxygen | facultatively anaerobic | facultatively anaerobic |

TABLE 5-continued

Microbiological characteristics of RK - 1 strain and MK - 1 strain

| Test item | Test result | |
|---|---|---|
| | RK - 1 | MK - 1 |
| Catalase | + | + |
| Growth under an anaerobic condition | + | + |
| V - P reaction | − | − |
| pH of V - P broth | 5.5 | 5.5 |
| Formation of acid from glucose | + | + |
| Formation of gas from glucose | − | − |
| Liquefaction of gelatin | − | − |
| Decomposition of starch | + | + |
| Utilization of citrate salt | − | − |
| Utilization of propionate salt | − | − |
| Yolk reaction | − | − |
| Reduction of nitrate salt | + | + |
| Growth at pH 6.8*1 | + | + |
| Growth at pH 5.7*1 | − | + |
| Growth in the presence of 5% NaCl | + | + |
| Growth in the presence of 7% NaCl | − | + |
| Growth at 30° C. | + | + |
| Growth at 55° C. | + | + |
| Growth at 65° C. | − | − |
| GC content of intracellular DNA (mol %) | 38 | 46 |

*1Nutrient broth was used

TABLE 7

Inhibitor
(Heat resistant trehalose phosphorylase)

| Inhibitor* | Relative activity (%) |
|---|---|
| $FeCl_2$ | 96 |
| $MgCl_2$ | 103 |
| $MnSO_4$ | 108 |
| $CaCl_2$ | 102 |
| $Pb(CH_3COO)_2$ | 93 |
| $Ba(OH)_2$ | 106 |
| $ZnSO_4$ | 20 |
| $CuSO_4$ | 89 |
| $HgCl_2$ | 1 |
| EDTA | 99 |
| DTT | 86 |
| PCMB | 0 |
| β - Mercaptoethanol | 96 |
| No addition | 100 |

*1 mM

TABLE 8

| | | Reaction conditions | | | 72 hours | | | | 144 hours | | | |
|---|---|---|---|---|---|---|---|---|---|---|---|---|
| No | Substrate (w/w %) | Amount of enzyme (U/g) | Temperature (°C.) | pH | Phosphoric acid (mM) | Maltose | Trehalose | Glucose | β-GIP (w/w %) | Maltose | Trehalose | Glucose | β-GIP (w/w %) |
| 1 | 30 | 10 | 60 | 5.0 | 5 | 11.5 | 15.4 | 0.8 | 0.0 | 10.3 | 16.6 | 1.0 | 0.0 |
| 2 | 30 | 10 | 60 | 5.0 | 10 | 11.1 | 19.1 | 0.9 | 0.1 | 9.4 | 18.6 | 1.2 | 0.1 |
| 3 | 30 | 10 | 60 | 5.0 | 25 | 11.0 | 18.5 | 1.1 | 0.1 | 10.8 | 19.3 | 1.3 | 0.1 |
| 4 | 30 | 10 | 65 | 5.5 | 10 | 9.9 | 15.6 | 0.9 | 0.1 | 10.4 | 16.1 | 1.0 | 0.1 |
| 5 | 30 | 10 | 65 | 5.5 | 25 | 10.2 | 17.0 | 1.3 | 0.1 | 10.4 | 17.2 | 1.5 | 0.1 |
| 6 | 20 | 5 | 65 | 5.5 | 25 | 7.7 | 11.1 | 0.7 | 0.1 | 9.5 | 11.8 | 0.9 | 0.2 |
| 7 | 20 | 3.5 | 65 | 5.5 | 25 | 8.8 | 9.1 | 0.6 | 0.2 | 9.4 | 10.8 | 0.9 | 0.2 |
| 8 | 20 | 1 | 65 | 5.5 | 25 | 16.0 | 3.6 | 0.5 | 0.4 | 15.2 | 4.4 | 0.5 | 0.4 |
| 9 | 20 | 3.5 | 65 | 5.0 | 25 | 10.6 | 9.3 | 0.6 | 0.3 | 10.7 | 9.9 | 0.8 | 0.2 |
| 10 | 20 | 3.5 | 65 | 6.0 | 25 | 7.7 | 8.4 | 1.2 | 0.2 | 7.4 | 9.2 | 1.3 | 0.1 |
| 11 | 20 | 3.5 | 70 | 5.5 | 25 | 10.4 | 7.5 | 0.6 | 0.3 | 8.3 | 7.8 | 0.8 | 0.2 |
| 12 | 20 | 3.5 | 70 | 6.0 | 25 | 8.2 | 8.0 | 1.1 | 0.6 | 8.0 | 8.4 | 0.8 | 0.2 |
| 13 | 20 | 3.5 | 70 | 6.0 | 50 | 9.5 | 8.5 | 1.0 | 0.5 | 7.4 | 8.6 | 1.2 | 0.3 |
| 14 | 20 | 3.5 | 70 | 6.0 | 150 | 7.9 | 6.9 | 1.4 | 1.1 | 7.3 | 7.6 | 1.7 | 0.7 |
| 15 | 20 | 3.5 | 70 | 6.0 | 300 | 9.6 | 5.9 | 1.8 | 1.7 | 9.2 | 8.2 | 2.2 | 1.1 |

TABLE 6

Substrate specificity
(Heat resistant trehalose phosphorylase)

| Substrate | Relative activity (%) |
|---|---|
| Trehalose | 100 |
| Neotrehalose | 1 |
| Maltose | 1 |
| Lsomaltose | 3 |
| Cellobiose | 2 |
| Sucrose | 1 |
| p - Nitrophenyl - α - D - glucoside | 2 |
| p - Nitrophenyl - β - D - glucoside | 2 |

What is claimed is:

1. Isolated heat resistant maltose phosphorylase having the following enzymological properties:

(a) action
  phosphorolyze maltose reversibly which when it is made to act on maltose in the presence of phosphoric acid, it produces glucose and β-glucose-1-phosphoric acid in an equimolar amount, and when it is made to act on glucose and β-glucose-1-phosphoric acid, it produces maltose and phosphoric acid in an equimolar amount, (b) substrate specificity
  acts specifically on maltose, (c) optimum temperature
  the optimum temperature of maltose phosphorolysis reaction is from about 55° C. to about 70° C., and it exhibits about 50% or more of the maximum activity in the range of 50° C. to 70° C., (d) thermal stability
the enzyme retains at least 80% of its activity after being subjected to a temperature of from 50° to 60° C. for 15 minutes in a buffer at pH 6.0, (e) optimum pH
6.0 to 7.0, (f) pH stability
stable at pH 5.5 to 8.0, and (g) molecular weight
150,000 to 190,000 when measured by gel filtration chromatography.

2. Isolated heat resistant maltose phosphorylase having the following enzymological properties:

(a) action
phosphorolyze maltose reversibly which when it is made to act on maltose in the presence of phosphoric acid, it produces glucose and β-glucose-1-phosphoric acid in an equimolar amount, and when it is made to act on glucose and β-glucose-1-phosphoric acid, it produces maltose and phosphoric acid in an equimolar amount, (b) substrate specificity
act specifically on maltose, (c) optimum temperature
the optimum temperature of maltose phosphorolysis reaction is from about 55° C. to about 70° C., and it exhibits about 50% or more of the maximum activity in the range of 5°° C. to 70° C., (d) thermal stability
the enzyme retains at least 80% of its activity after being subjected to a temperature of from 50° to 60° C. for 15 minutes in a buffer at pH 6.0, (e) optimum pH
6.0 to 7.0, (f) pH stability
stable at pH 5.5 to 8.0, (g) molecular weight
150,000 to 190,000 when measured by gel filtration chromatography, (h) inactivation
100% inactivated when heated at 100° C. for 10 minutes, (i) isoelectric point
4.7 to 5.1, and (j) inhibitor
its activity is 99% inhibited with 1 mM $HgCl_2$.

* * * * *